US 6,666,873 B1

(12) United States Patent
Cassell

(10) Patent No.: US 6,666,873 B1
(45) Date of Patent: Dec. 23, 2003

(54) SURGICAL COUPLER FOR JOINING TUBULAR AND HOLLOW ORGANS

(76) Inventor: Jack L. Cassell, 18526 C.R. 44A, Eustis, FL (US) 32736

( * ) Notice: Subject to any disclaimer, the term of this patent is extended or adjusted under 35 U.S.C. 154(b) by 0 days.

(21) Appl. No.: 10/289,675

(22) Filed: Nov. 7, 2002

Related U.S. Application Data

(60) Provisional application No. 60/401,522, filed on Aug. 8, 2002.

(51) Int. Cl.[7] ............................................. A61B 17/08
(52) U.S. Cl. ..................................... 606/153; 606/213
(58) Field of Search ............................ 606/153, 213, 606/217, 151; 411/427, 429; 24/572, 578

(56) References Cited

U.S. PATENT DOCUMENTS

| | | | |
|---|---|---|---|
| 4,055,186 A | 10/1977 | Leveen | |
| 4,552,148 A | 11/1985 | Hardy, Jr. | |
| 4,598,712 A | 7/1986 | Rebuffat | |
| 4,693,249 A | * 9/1987 | Schenck et al. | ............ 606/153 |
| 4,708,141 A | 11/1987 | Inoue | |
| 4,752,024 A | 6/1988 | Green | |
| 4,873,977 A | 10/1989 | Avant | |
| 4,917,087 A | * 4/1990 | Walsh et al. | ............... 606/153 |
| 4,931,057 A | 6/1990 | Cummings | |
| 4,966,602 A | 10/1990 | Rebuffat | |
| 5,035,702 A | * 7/1991 | Taheri | ......................... 606/153 |
| 5,047,039 A | 9/1991 | Avant | |
| 5,234,448 A | * 8/1993 | Wholey et al. | ............. 606/153 |
| 5,250,058 A | 10/1993 | Miller | |
| 5,346,501 A | 9/1994 | Regula | |
| 5,503,635 A | 4/1996 | Sauer | |
| 5,540,701 A | 7/1996 | Sharkey | |
| 5,695,504 A | 12/1997 | Gifford, III | |
| 6,350,280 B1 | 2/2002 | Nash | |
| 6,391,036 B1 | 5/2002 | Berg | |
| 6,461,367 B1 | 10/2002 | Kirsch | |
| 2002/0077661 A1 | 6/2002 | Saadat | |
| 2002/0099393 A1 | 7/2002 | Fleischman | |

* cited by examiner

Primary Examiner—Julian W. Woo
(74) Attorney, Agent, or Firm—John V. Stewart

(57) ABSTRACT

A surgical coupler with two short tubular components that snap together. Each component has semi-flexible barbed spokes radiating from the exterior surface at one end of the tube. The spokes are held temporarily against the exterior of each component by a removable sleeve. Each component and sleeve is inserted into one of two respective organic tubular openings to be joined. The sleeve is removed, and the component is turned in a given angular direction and amount. The spokes expand radially into the tissue of each organ, fixing the component in the opening. The couplers are then pressed together using a hollow catheter and a tractor catheter, connecting them. They hold the tissue openings in alignment and abutment for healing, and provide a fluid communication channel with a liquid-tight seal while the couplers are bio-absorbed.

5 Claims, 5 Drawing Sheets

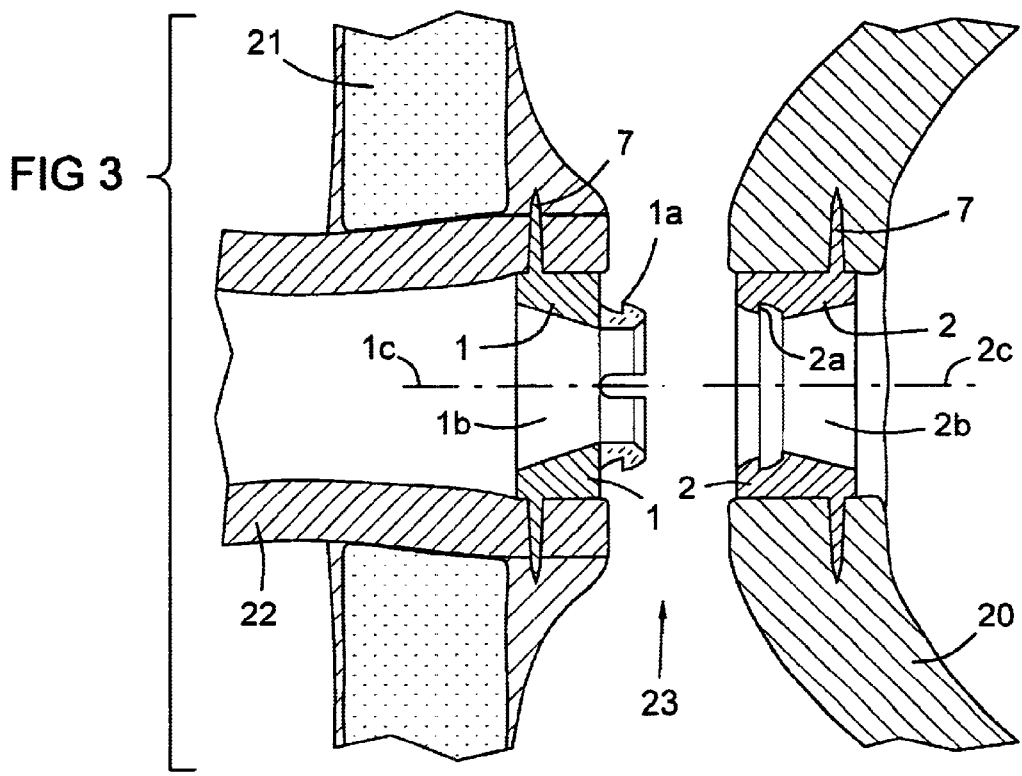
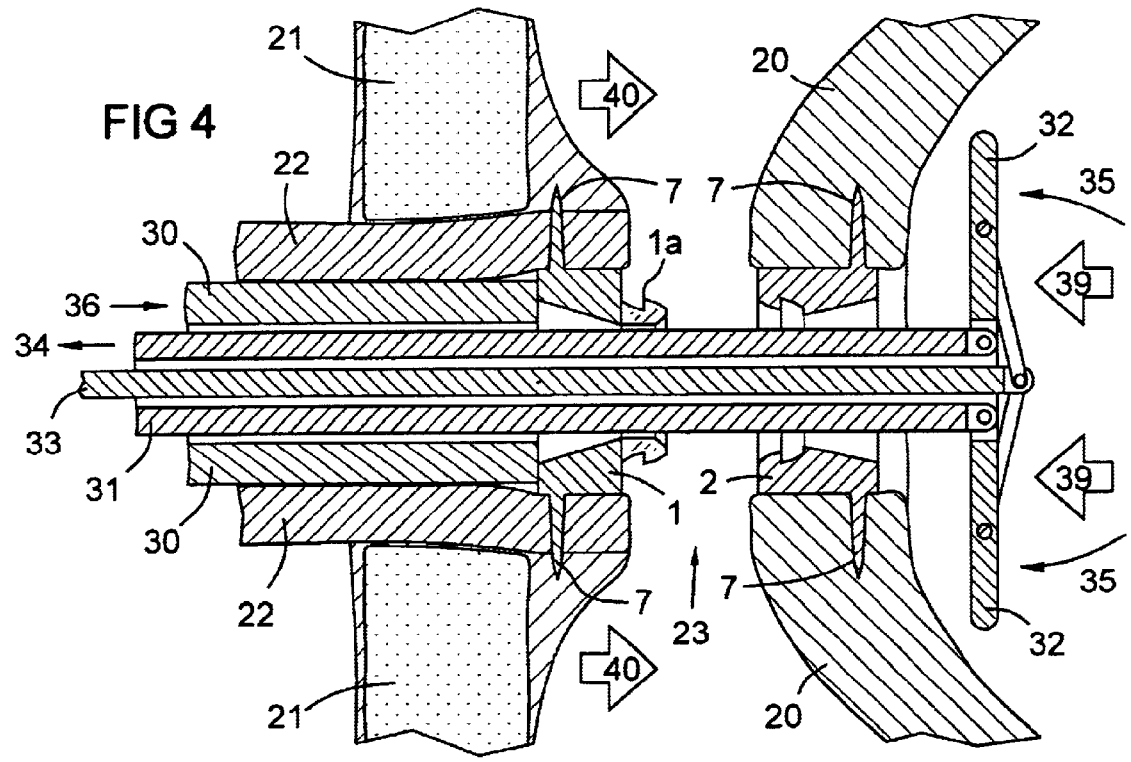

SURGICAL COUPLER FOR JOINING TUBULAR AND HOLLOW ORGANS

CROSS-REFERENCE TO RELATED APPLICATIONS

This application claims the benefit of provisional patent application No. 60/401,522, filed Aug. 8, 2002.

BACKGROUND OF THE INVENTION

1. Field of the Invention

This invention relates to surgical coupling devices for joining tubular and hollow organs such as joining the urethra to the bladder after a radical prostatectomy.

2. Description of Prior Art

Prior patents and patent applications show numerous fixtures for surgically connecting tubular and hollow organs. These include fixtures for joining a graft vessel to a blood vessel, and for joining the urethra to the bladder after prostate removal.

US 2002/0077661 (Saadat) shows a tubular connector with sharp external spikes angled toward the middle of the tube that penetrate tissue for connecting tubular body organs.

U.S. Pat. No. 6,391,036 (Berg) shows a tubular connector with radial fingers at one or both ends. The fingers may be sharp and barbed to penetrate tissue. A delivery tube depresses the fingers for insertion through the wall of a body conduit. However, these fingers do not expand within a plane normal to the axis of the coupling tube as in the present invention. They do not penetrate the sides of the opening radially as in the present invention. Instead, they open from an orientation in line with the periphery of the coupler to rest against the inner wall of the organ, and optionally against the outer wall as well. One of the tubular organs must be attached to the coupler by sutures, unlike the present invention.

U.S. Pat. No. 6,350,280 (Nash) shows an anastomosis coupler with two halves that snap together.

U.S. Pat. No. 5,695,504 (Gifford) shows numerous anastomosis fixtures with sharp fingers that penetrate tissue in various ways. One version has staple fingers that penetrate the side of a tubular organ with a twist motion. However, these fingers are oriented in line with the periphery of the fixture rather than radially as in the present invention. They penetrate the exterior of a hollow organ around an opening rather than expanding radially outward along a plane into the sides of an opening as in the present invention. Gifford requires a second set of counter-rotating fingers to lock it, unlike the present invention.

U.S. Pat. No. 5,503,635 (Sauer) shows male and female coupler components that are inserted in the ends of a tubular organ, fixed to the tissue, then snapped together However, none of the prior devices provide a two-part snap coupler with sharp spokes on each part that expand radially with a twist into the interior wall of a tubular organ and the wall of the opening of a hollow organ, as does the present invention. The present invention is uniquely simple to use, stable and secure, quick and sure to apply, and it does not reduce tissue by overlapping or trimming, as do several of the prior devices. The present invention simply brings the tissue openings in alignment and abutment, without overlap or extra trimming.

SUMMARY OF THE INVENTION

An object of the invention is provision of a surgical coupler for joining tubular and hollow organs in a fluid-tight junction with fluid communication between the organs, without sutures, quickly and securely. Another object is to bring together and hold the tissues to be joined in optimum alignment. Another object is to bring the tissues to be joined in direct abutment, without overlapping the tissues or extra trimming, to avoid unnecessary length reduction and tension on the tissues. Another object is to provide a usable fluid communication channel between joined organs while healing proceeds. Another object is elimination of a secondary operation to remove sutures or fixtures. Another object is to minimize invasion, modification, and irritation of surrounding tissues.

These objectives are met in a surgical coupler with two short tubular components that snap together. Each component has semi-flexible barbed spokes radiating from the exterior surface at one end of the tube. The spokes are held temporarily against the exterior of each component by a removable sleeve. Each component and sleeve is inserted into one of two respective organic tubular openings to be joined. The sleeve is removed, and the component is manually turned about its axis in a given angular direction and amount. The spokes expand radially into the tissue of each organ, fixing the component in the opening. The couplers are then pressed together using a hollow catheter and a tractor catheter, connecting them. They hold the tissue openings in alignment and abutment for healing, and provide a fluid communication channel with a liquid-tight seal while the couplers are bio-absorbed.

BRIEF DESCRIPTION OF THE DRAWINGS

FIG. 3 is a side sectional view of the surgical coupler installed in the urethra and the bladder for joining (anastomosis) after radical prostatectomy.

FIG. 4 is a side sectional view of as in FIG. 3 with catheters inserted for pushing the two coupler components together.

REFERENCE NUMBERS

Figure 1:
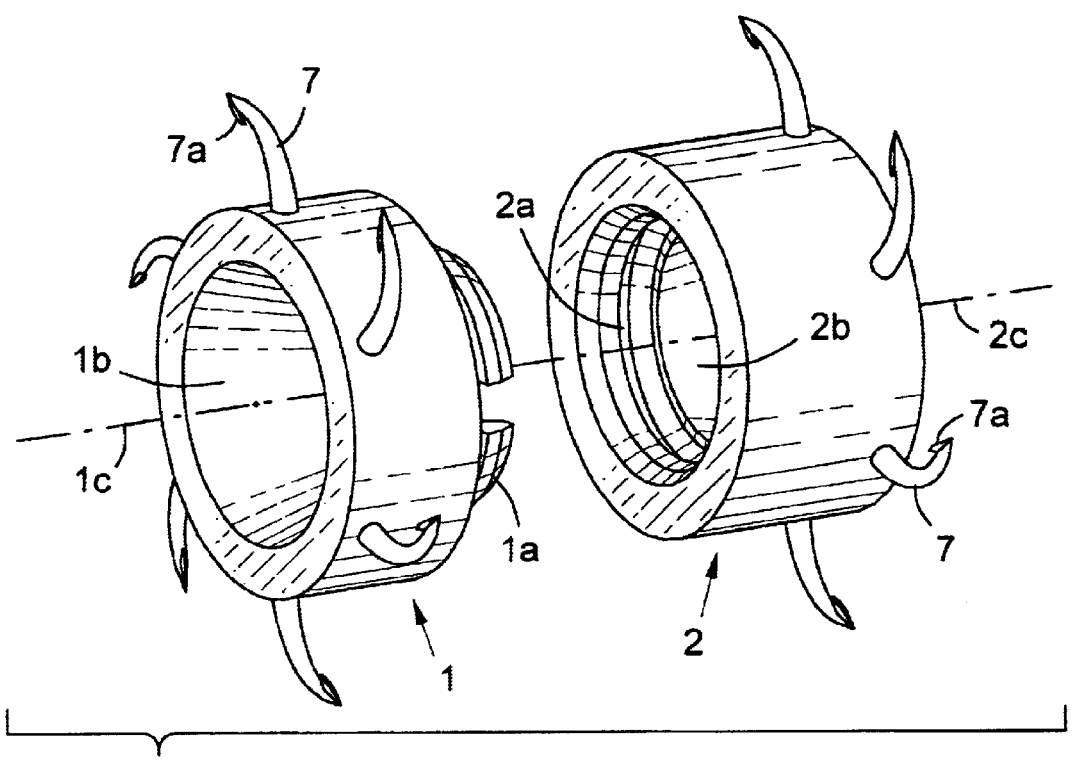
FIG. 1 is an exploded perspective view of a surgical coupler according to the invention.
Figure 2:
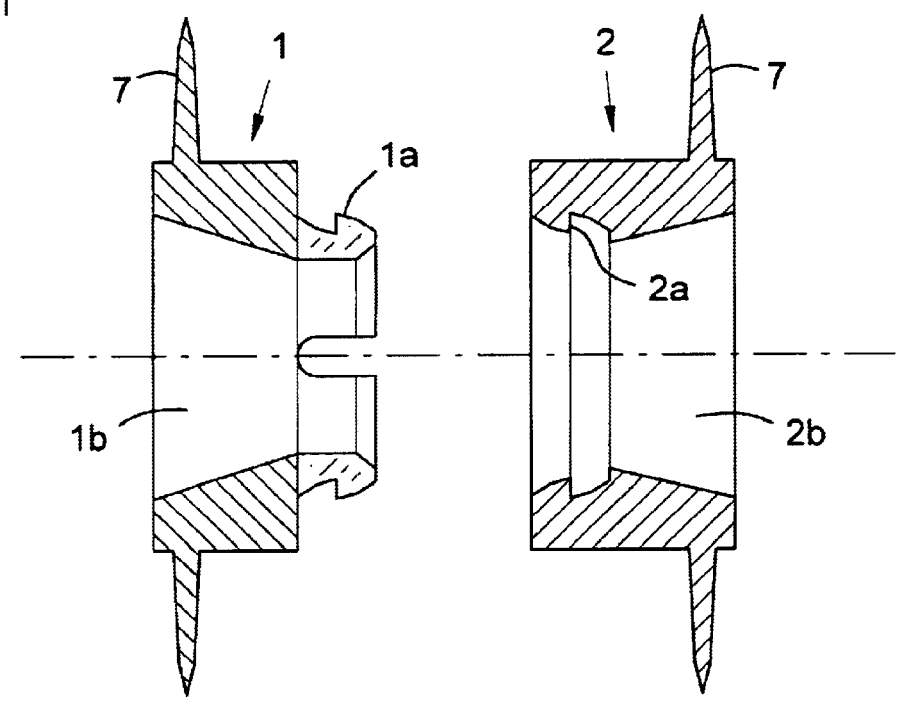
FIG. 2 is a side sectional view of the surgical coupler of FIG. 1.
Figure 5:
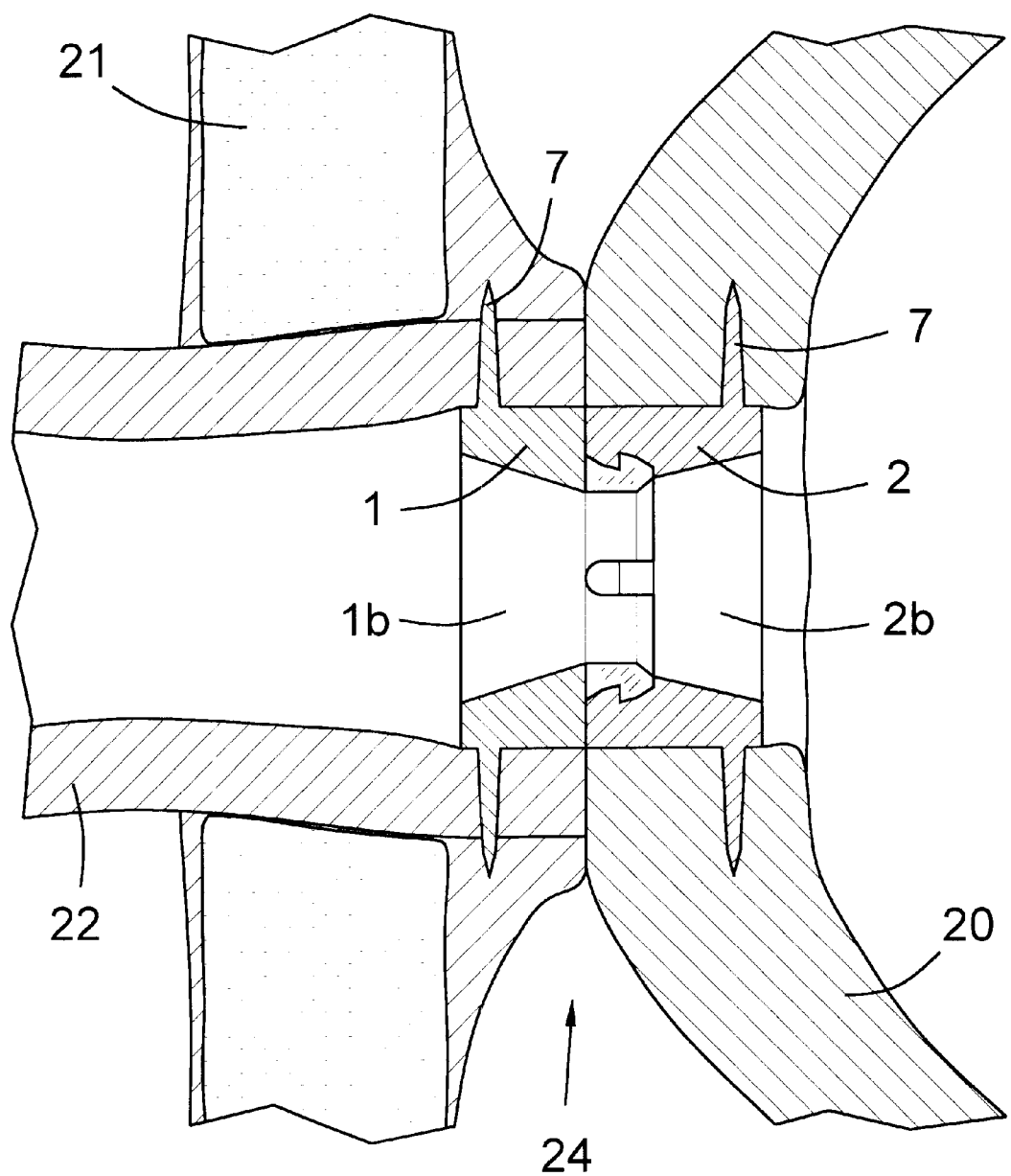
FIG. 5 is a side sectional view of an anastomosis formed with the surgical coupler.

1. First coupler component
1a. First interconnection device
1b. Passage of first coupler component
1c. Axis of first coupler component
2. Second coupler component
2a. Second interconnection device
2b. Passage of second coupler component 2c. Axis of second coupler component
3. Sleeve for first coupler component
4. Sleeve for second coupler component
7. Spoke
7a. Barb
20. Urinary bladder wall
21. Urinary sphincter muscle
22. Urethra
23. Prostate removal site
24. Anastomosis
30. Hollow catheter, such as a Van Buren catheter
31. Tractor catheter, such as a Lowsley Tractor
32. Wings on Tractor catheter head
33. Control rod in tractor catheter
34. Force direction on Lowsley Tractor catheter
35. Deployment direction of wings on Lowsley Tractor head
36. Force direction on Van Buren catheter
39. Motion of tractor head after wing deployment, relative to Van Buren catheter, which forces the coupler components together.
40. Motion of Van Buren catheter relative to tractor head, which forces the coupler components together.

TERMINOLOGY

Anastomosis: a joining of two organs that normally are not connected. For example, joining the urethra directly to the bladder after prostate removal.

DETAILED DESCRIPTION

The invention is a coupler for joining tubular and other hollow body organs cut by surgery. It is intended especially for rejoining the urinary bladder to the urethra after prostate gland removal. It is faster, easier, and more reliable than sutures, and provides a smoothly aligned, liquid-tight connection with less training and less manual dexterity than with suturing.

The result is a joining of the organs, or anastomosis, such that they heal together and form an organic fluid communication channel. The coupler is bioabsorbable, so it dissolves as the tissue seam heals. In the meantime, it holds the organic junction together and provides a liquid-tight fluid communication channel.

Figure 6:
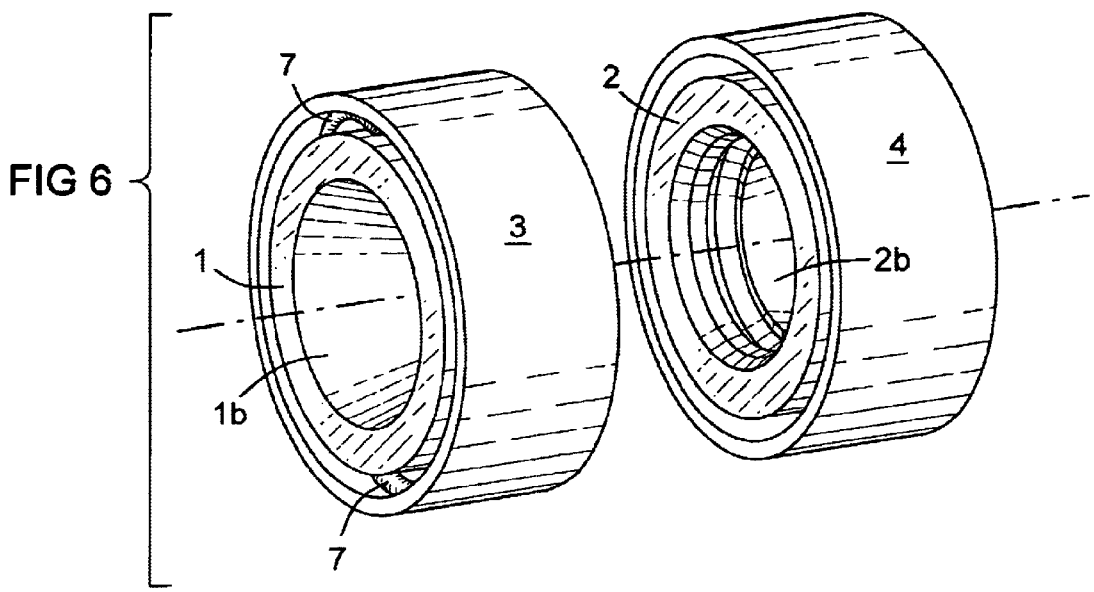
FIG. 6 is a perspective view of the surgical coupler ensleeved for insertion of the first and second coupler components into the urethra and bladder openings respectively.
Figure 7:
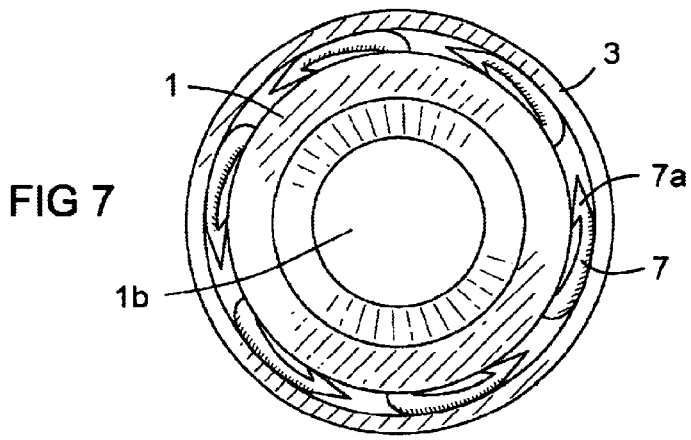
FIG. 7 is a front or distal view of the first component of the surgical coupler ensleeved as in FIG. 6.
Figure 8:
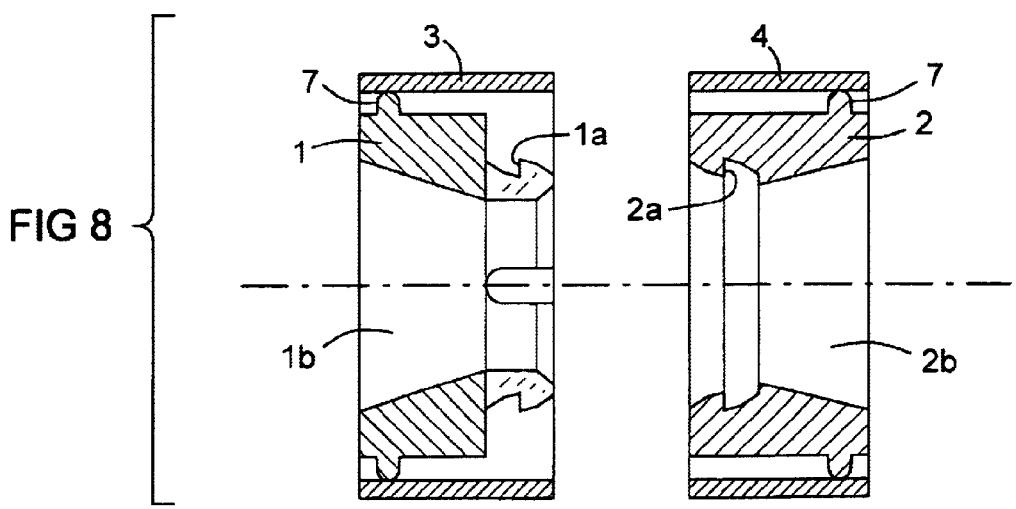
FIG. 8 is a side sectional view of the surgical coupler ensleeved as in FIG. 6.

The coupler includes a first component 1 and a second component 2. These are each short tubes with semi-flexible spokes 7 extending generally radially from them. The spokes preferably terminate with barbs 7a. The spokes are flexible enough to lie flat against the exterior surface of the respective coupler component. The spokes are held in this retracted position by sleeves 3 and 4, as shown in FIGS. 6–8.

Figure 9:
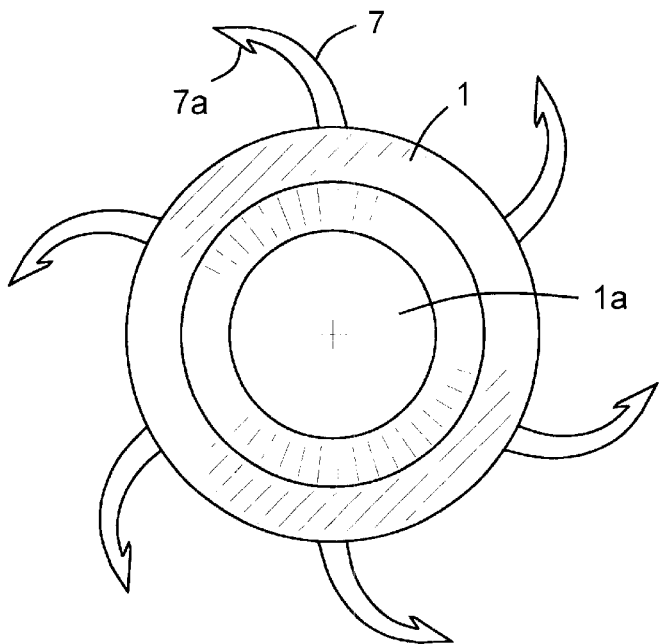
FIG. 9 is a front or distal view of first component of the surgical coupler with semi-flexible spokes partially deployed as during installation by twisting the coupler component in a tissue opening.
Figure 10:
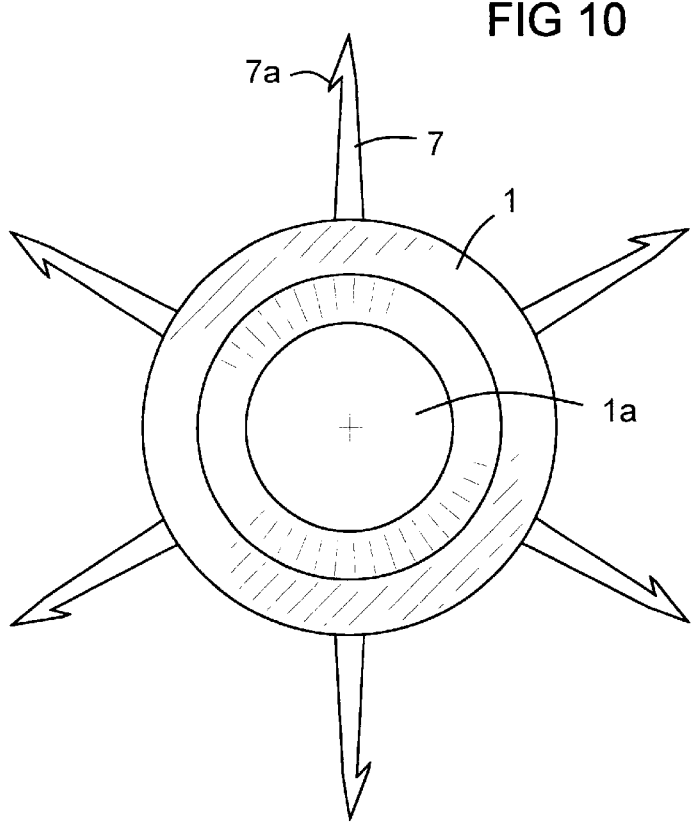
FIG. 10 is a front or distal view of first component of the surgical coupler with spokes fully deployed.

The first coupler 1 and its sleeve 3 are inserted into the severed proximal end of the urethra 22. The sleeve 3 is then removed, and the coupler 1 is rotated to expand the spokes 7, and drive them into the tissue of the urethra. The spokes expand as shown in FIG. 9, up to a maximum expansion as shown in FIG. 10, as the coupler is turned through a specified angular amount and direction. This fixes the first coupler in the severed end of the urethra. The second coupler is likewise inserted in the opening in the bladder 20 and is fixed by removing the sleeve 4 and rotating the coupler.

The couplers are designed to snap together via interconnection devices 1a and 1b. For example, a protruding lip 1a is shown on the first coupler, and a circular receiving lip 2a in the second coupler. The protruding lip 1a can be segmented if desired for increased flexibility. An O-ring of an elastic bioabsorbable material can be retained behind the lip 1a as a gasket between the couplers if desired for improved sealing.

To push the two coupler halves together, a hollow catheter 30, such as a Van Buren catheter, is inserted through the urethra 22 via the natural opening in the penis until it contacts the male coupler 1. A tractor catheter, such as a Lowsley tractor, is inserted through the first catheter, through both coupler components and into the bladder. The tractor catheter has a tip 32 that spreads under manual control from outside the penis. The tractor catheter is then pulled back, causing the tractor tip to push the second component of the coupler against the first component, engaging them. Then the tractor tip 32 is reduced to its minimal size by external manipulation of the control rod 33, and the catheters are withdrawn. The result is as shown in FIG. 4, with the severed surfaces of the urethra and bladder held directly together with mucosa-to-mucosa alignment. This tissue seam heals while the couplers dissolve.

A semi-flexible bioabsorbable material known in the surgical suture and fixture arts such as polydioxanone can be used for the couplers and spokes. The angular direction of bending of the spokes on the first and second coupler components may be the same or different. Preferably the spokes are angled such that each component is installed with a clockwise twist. The spokes may optionally be mounted on the coupler components by a hinge at the base of each spoke (not shown) that allows the spoke to fold in the desired direction and deploy to a stop at the radial orientation.

Although the present invention has been described herein with respect to preferred embodiments, it will be understood that the foregoing description is intended to be illustrative, not restrictive. Modifications of the present invention will occur to those skilled in the art. All such modifications that fall within the scope of the appended claims are intended to be within the scope and spirit of the present invention.

I claim:

1. A surgical coupler for joining tubular and hollow organs, comprising;
   a first generally tubular component having a first axis and two open ends;
   a second generally tubular component having a second axis and two open ends;
   interconnection means on the first and second tubular components for quickly connecting them end-to-end generally coaxially by pressure in an axial direction to form a combined generally tubular shape;
   the first tubular component having an exterior surface with a first set of semi-flexible barbed spokes extending generally radially in a first plane generally normal to the first axis;
   the second tubular component having an exterior surface with a second set of semi-flexible barbed spokes extending generally radially in a second plane generally normal to the second axis;
   a first removable sleeve for temporarily holding the first set of spokes bent against the exterior of the first tubular component in a first common angular direction generally in said first plane;
   a second removable sleeve for temporarily holding the second set of spokes bent against the exterior of the second tubular component in a second common angular direction generally in said second plane.

2. A method of joining an open end of a tubular organ to an opening in a hollow organ, comprising the steps of:
   providing a surgical coupler as in claim 1;
   installing the first sleeve on the first tubular component, compressing the first set of spokes in a first common angular direction generally in said first plane;

installing the second sleeve on the second tubular component, compressing the second set of spokes in a second common angular direction generally in said second plane;

inserting the first tubular component and first sleeve in the open end of the tubular organ;

removing the first sleeve from the first tubular component;

turning the first tubular component in said first common angular direction, expanding the first set of spokes into the interior wall of the tubular organ;

inserting the second tubular component and second sleeve in the opening of the hollow organ;

removing the second sleeve from the second tubular component;

turning the second tubular component in said second common angular direction, expanding the second set of spokes into the wall of the opening in the hollow organ;

pressing the first and second tubular components together, engaging the interconnection means, and connecting them end-to-end.

3. A surgical coupler for joining tubular and hollow organs, comprising a first coupler component having a generally cylindrical exterior, a first axis, an axial passage, a first end, and a second end;

a first set of sharp spokes arrayed around the exterior of the first end of the first coupler component in approximately a radial orientation in approximately a first plane normal to the first axis, each of the first set of spokes foldable against the exterior of the first coupler in a first common circumferential direction in approximately said first plane, at least some of said first set of spokes having a barbed tip;

a removable sleeve surrounding the first coupler and holding the first set of spokes in a folded position in the first common direction;

a first interconnection device on the second end of the first coupler component;

a second coupler component having a generally cylindrical exterior, a second axis, an axial passage, a first end and a second end;

a second set of sharp spokes arrayed around the exterior of the second end of the second coupler component in approximately a radial orientation in approximately a second plane normal to the second axis, each of the second set of spokes foldable against the exterior of the second coupler in a second common circumferential direction in approximately said second plane, at least some of said second set of spokes having a barbed tip;

a removable sleeve surrounding the second coupler and holding the second set of spokes in a folded position in the second common direction;

a second interconnection device on the first end of the second coupler component;

the first and second interconnection devices having a mating interface for joining the first and second coupler components end-to-end, approximately coaxially with each other, with an axial passage through the two joined components.

4. The surgical coupler of claim 3, wherein the spokes are semi-flexible, fold against the exterior of the respective coupler component by flexing, and deploy elastically to approximately a radial orientation.

5. The surgical coupler of claim 3, wherein all materials of the coupler are bioabsorbable.

* * * * *